United States Patent [19]

Bergfeld et al.

[11] Patent Number: 5,478,950
[45] Date of Patent: Dec. 26, 1995

[54] PROCESS FOR PRODUCING PYRROLIDONE AND N-ALKYL PYRROLIDONES

[75] Inventors: Manfred Bergfeld, Erlenbach-Mechenhard; Gunter Wiesgickl, Grosswallstadt, both of Germany

[73] Assignee: Akzo Nobel N.V., Arnhem, Netherlands

[21] Appl. No.: 284,545

[22] PCT Filed: Feb. 3, 1993

[86] PCT No.: PCT/EP93/00239

§ 371 Date: Aug. 8, 1994

§ 102(e) Date: Aug. 8, 1994

[87] PCT Pub. No.: WO93/16042

PCT Pub. Date: Aug. 19, 1993

[30] Foreign Application Priority Data

Feb. 7, 1992 [DE] Germany ............... 42 03 527.9

[51] Int. Cl.$^6$ ............... C07D 201/08; C07D 207/267
[52] U.S. Cl. ............... 548/552; 548/554
[58] Field of Search ............... 548/552, 557

[56] References Cited

U.S. PATENT DOCUMENTS

| | | | |
|---|---|---|---|
| 2,267,757 | 12/1941 | Schuster et al. | 260/313 |
| 3,109,005 | 10/1963 | Lidov | 260/326.5 |
| 3,115,500 | 12/1963 | Dunlop et al. | 260/326.5 |
| 3,136,780 | 6/1964 | Kolyer et al. | 260/326.5 |
| 3,198,808 | 8/1965 | Himmele et al. | 260/326.5 |
| 3,235,562 | 2/1966 | Shilling | 260/326.3 |
| 3,448,118 | 6/1969 | Chichery et al. | 260/326.5 |
| 3,775,431 | 11/1973 | Roderwald, Jr. | 260/326.5 PL |
| 3,884,936 | 5/1975 | Hollstein | 260/326.5 FN |
| 4,885,371 | 12/1989 | Tracy et al. | 548/554 |
| 5,101,045 | 3/1992 | Koehler et al. | 548/554 |

FOREIGN PATENT DOCUMENTS

| | | |
|---|---|---|
| 931685 | 7/1963 | European Pat. Off. . |
| 1109540 | 4/1968 | European Pat. Off. . |
| 0184055 | 6/1986 | European Pat. Off. . |
| 0464359A2 | 1/1992 | European Pat. Off. . |
| 1576183 | 7/1969 | France . |
| 2159859 | 7/1972 | Germany . |
| 2200600 | 8/1972 | Germany . |
| 47-21420 | 10/1972 | Japan . |
| 49-259 | 1/1974 | Japan . |
| 49-20485 | 2/1974 | Japan . |
| 51-42107 | 4/1976 | Japan . |
| 1-186863 | 7/1989 | Japan . |
| 1-190667 | 7/1989 | Japan . |
| 1-186864 | 7/1989 | Japan . |
| 143806 | 11/1962 | U.S.S.R. . |
| 192820 | 3/1967 | U.S.S.R. . |
| 259889 | 12/1969 | U.S.S.R. . |
| 1558903 | 4/1990 | U.S.S.R. . |
| WO86/07358 | 12/1986 | WIPO . |

OTHER PUBLICATIONS

"Synthetic zeolites as Catalysts for the Ring Conversion of gamma-Butyrolactone into 1-substituted 2-Pyrrolidones" Bulletin of the Chemical Society of Japan, Bd. 50 Nr. 10, Oct. 1977, Tokyo Japan, pp. 2517–2521.

"Ring Transformations of gamma-Butyrolactone into 2-Pyrrolidone over Zeolites", Hatada et al., Journal of Catalysis, 1975, pp. 166–175.

"Ring Transformations of Oxygen Containing Heterocycles Into Nitrogen Containing Heterocycles over Synthetic Zeolties", Hatada et al., Chemistry Letters, 1974, pp. 439–442.

*Primary Examiner*—David B. Springer
*Attorney, Agent, or Firm*—Oliff & Berridge

[57] ABSTRACT

The invention relates to a process for producing pyrrolidone and N-alkyl pyrrolidones from saturated or unsaturated 1,4-dicarboxylic acids or their anhydrides, hydrogen, and a primary amine, characterized in that the dicarboxylic acid or its anhydride is allowed to react in an appropriate reactor with hydrogen or ammonia via a first catalyst bed and the unisolated intermediate product is subsequently reacted with the primary amine or ammonia directly via a second, downstream catalyst bed.

16 Claims, No Drawings

PROCESS FOR PRODUCING PYRROLIDONE AND N-ALKYL PYRROLIDONES

FIELD OF THE INVENTION

The application relates to a process for producing pyrrolidone and N-alkyl pyrrolidones from saturated or unsaturated 1,4-dicarboxylic acids and their anhydrides; hydrogen; and a primary amine or ammonia.

BACKGROUND

N-alkyl pyrrolidones, particularly N-methylpyrrolidone, are technically very important solvents in industrial petrochemistry and are also used as starting substances for various syntheses.

N-methylpyrrolidone is generally produced industrially using the Reppe process (Chem. Ing. Technik (22) 17, 1950, pp. 361 ff.), in which monomethylamine and gamma-butyrolactone are maintained with a suitable diluent for a certain period of time at temperatures exceeding 250° C. and reacted with each other via a dehydrating catalyst. Due to the freely occurring dimerization of N-methylpyrrolidone as a result of the reaction, the yield is only 85–90%, however.

In U.S. Pat. No. 4,885,371, a process for producing N-methylpyrrolidone is described in which monomethylamine and gamma-butyrolactone are reacted with each other via a borohydride catalyst.

A number of other publications (JP 01-190667, JP 01-186864, JP 01-186863) also describe the synthesis of N-alkyl pyrrolidones, starting from gamma-butyrolactone, with primary, secondary, or tertiary amines. The mean reaction time is 3 h at 250° C.

According to the Soviet application no. 1558903, N-methylpyrrolidone is produced by reaction of gammabutyrolactone and an excess of monomethylamine at 250° C. via a Y zeolite as a catalyst. According to K. Hatada et al. (Bull. Chem. Soc. Japan .50(10), 1977, pp. 2517–2521), a copper-exchanged Y zeolite is used as a catalyst for the same reaction.

In the process of JP 49-020585, N-methylpyrrolidone is obtained by reaction of monomethylamine, diluted with a large amount of water, and gamma-butyrolactone at 250° C. and 2 hours reaction time.

The process of JP 51-042107 uses gammabutyrolactone, methylamine, and water in the ratio of 1:1.4:4 to produce N-methylpyrrolidone as the end product at a temperature of 250° C. and a pressure of 45–50 kg/cm$^2$. The excess water serves as a carrier for the reuse of unreacted methylamine.

In accordance with JP 49-000259, N-methylpyrrolidone is obtained by heating a mixture of gamma-butyrolactone, alkylamine, and hydrogen for 3 hours at 270° C. A mixture of copper and a metallic oxide (Cu Plus $SiO_2$, $Al_2O_3$, $SiO_2$-$Al_2O_3$, $TiO_2$, $ZrO_2$, or $Cr_2O_3$) is used as a catalyst. The reaction takes place in the gaseous phase, and the yield is only about 60%.

According to JP 47-021420, N-methylpyrrolidone is obtained with a yield of 99% when monomethylamine and gamma-butyrolactone are allowed to react with each other in the aqueous phase for a sufficient length of time.

JP 49-020582 describes a process in which monomethylamine is first allowed to react with gammabutyrolactone, followed by a cyclization, such as via an aluminum oxide catalyst.

Finally, DE 2200600 describes a process for producing N-methylpyrrolidone from maleic anhydride, hydrogen, and an amine compound, in which a palladium-carbon catalyst is used. A yield of only at most 78.4% is obtained at a reaction temperature of 275° C. and a pressure of 119 atm. The reaction occurs in an excess of water.

Furthermore, very long reaction times are prescribed and the reaction occurs under very high pressure, so that expensive process-related measures are needed.

All the aforementioned processes have the disadvantage either that the yield is low or that the product is unsatisfactorily impure and must undergo expensive purification following the process. In a manner similar to that described in DE-A 2200600, processes are also disclosed in U.S. Pat. No. 3,109,005, U.S. Pat. No. 3,448,118, and U.S. Pat. No. 3,198,808 in which pyrrolidone or pyrrolidones are produced using a so-called one-vessel process. These processes have the disadvantages previously mentioned. However, the synthesis usually starts from gamma-butyrolactone, which must be previously produced from 1,4-butanediol, maleic anhydride, or other educts, and isolated.

The object of the invention, therefore, is to provide a process in which N-alkyl pyrrolidones or pyrrolidone itself can be produced directly from the corresponding dicarboxylic acids or their anhydrides, without the otherwise common isolation of an intermediate product, and in which a high product yield is achieved while at the same time fulfilling the high purity requirements imposed on the product.

SUMMARY OF THE INVENTION

This object is met in accordance with the invention by allowing the dicarboxylic acids or their anhydrides to react with hydrogen in a suitable reactor via a first catalyst bed and subsequently reacting the unisolated intermediate product with a primary amine or ammonia via a second catalyst bed downstream from the first.

DETAILED DESCRIPTION OF PREFERRED EMBODIMENTS

In the process according to the invention, the corresponding intermediate product is first obtained downstream from or above the first catalyst bed, with a yield and purity up to 98% or more, and, then reacted, is then in the gaseous phase state, is then with the primary amine or ammonia above the second, downstream catalyst bed to form N-alkylpyrrolidone or pyrrolidone. In this second step as well, the purity and yield are each on the average up to 98% or more.

Use of a catalyst containing copper for the first catalyst bed has proven advantageous for the process.

Likewise, use of a catalyst containing silicon or an aluminum-phosphate catalyst for the second, downstream catalyst bed has proven advantageous for the process.

In particular, catalysts with a zeolitic structure are preferred. The best results, however, are obtained using a copper chromite catalyst for the first catalyst bed and a cation-exchanged zeolite of type X or Y for the second catalyst bed. With this combination, a conversion of the reactants of up to 98% or more is possible.

The reaction takes place preferably in the gaseous phase, in order to achieve optimum conversion of the reactants.

To enable better control of the reaction and sufficiently exact dosing of the reactants, diluents such as gases, water, or aprotic solvents can be present. It has proven advantageous for the reactants of the first step, especially for hydrogen, to be introduced to the reaction system after diluting with nitrogen. Likewise, the primary amine is easier to dose in a diluted, aqueous solution. Overall, by using the previously mentioned diluents a reaction is achieved that proceeds continuously.

The temperature inside the reactor is 225° to 350° C. above the first catalyst bed and 225° to 400° C. above the second catalyst bed, whereby 250° to 300° C. is preferred for the first catalyst bed and 260° to 340° C. for the second catalyst bed. Maximum space-time yields are obtained in this case.

The molar ratio of 1,4-dicarboxylic acid or its anhydride to hydrogen is from 1 to 20 to 1 to 250, whereas the molar ratio of hydrogen to the primary amine or ammonia is from 15 to 1 to 250 to 1.

The reaction is further characterized by short to very short retention times of the applicable reaction mixture above the respective associated catalyst bed. These times are 0.01 to 15 seconds in each case and can be reduced to times under 3 seconds by employing appropriate flow rates and reactant ratios.

The reaction can also be conducted advantageously when the reaction pressure is only within the range from 0.1 to 10 bar. In most cases, the general ambient pressure is not exceeded so that the reaction can be conducted using simple apparatus or reactors suitable for slight overpressure.

The product according to the invention can be obtained with a yield and purity of up to 98% or more and contains as byproducts only some gamma-butyrolactone and possibly propionic acid, both of which can be eliminated easily. Particularly when producing N-methylpyrrolidone from maleic acid, methylamine, and water, the unconverted gamma-butyrolactone is easily separated, since it is converted during the distillation to gamma-hydroxy N-methyl butylamide, which, together with other possible by-products, remains behind in the distillation residue.

The present invention is explained in more detail by the following example.

EXAMPLE 1

A conventional glass reactor is fitted with a feed opening at a suitable location between the first and second catalyst beds.

The catalyst for the first catalyst bed comprises 21.95 g Cu chromite catalyst (manufacturer: Alfa) and the catalyst for the second catalyst bed 15.9 g Nax zeolite.

1.584 mol/h hydrogen and 0.016 mol/h maleic anhydride were fed over the first catalyst bed and additionally 0.017 mol/h monomethylamine and 0.096 mol/h water through the reactor feed opening.

The temperature was 275° C. above the first catalyst bed and 275° above the second catalyst bed.

After a total reaction time of 4 hours, 6.09 g N-methylpyrrolidone is obtained. The yield is 96%.

We claim:

1. Process for producing pyrrolidone and N-alkyl pyrrolidones from saturated or unsaturated 1,4-dicarboxylic acids or their anhydrides; hydrogen; and a primary amine or ammonia, wherein said dicarboxylic acid or its anhydride is allowed to react in an appropriate reactor with hydrogen via a first catalyst bed and the unisolated intermediate product is subsequently reacted with the primary amine or ammonia via a second, downstream catalyst bed.

2. Process in accordance with claim 1, wherein a catalyst containing copper is used in the first catalyst bed.

3. Process in accordance with claim 1, wherein a catalyst containing silicon or an aluminum-phosphate catalyst is used in the second catalyst bed.

4. Process in accordance with claim 3, wherein said catalyst has a zeolitic structure.

5. Process in accordance with claim 1, wherein a copper chromite catalyst is used in the first catalyst bed and a cation-exchanged zeolite of type X or Y is used in the second catalyst bed.

6. Process in accordance with claim 1, wherein the reaction occur in the gaseous phase.

7. Process in accordance with claim 1, wherein the process further contains diluents.

8. Process in accordance with claim 7, wherein the diluent comprises gases, water, or aprotic solvents.

9. Process in accordance with claim 1, wherein the temperature inside the reactor above the first catalyst bed is 225° to 350° C.

10. Process in accordance with claim 1, wherein the temperature inside the reactor above the second catalyst bed is 225° to 400° C.

11. Process in accordance with claim 1, wherein the temperature is 250° to 300° C. above the first catalyst bed and 260° to 340° C. above the second catalyst bed.

12. Process in accordance with claim 1, wherein a molar ratio of 1,4-dicarboxylic acid or its anhydride to hydrogen is from 1 to 20 to 1 to 250.

13. Process in accordance with claim 1 wherein a molar ratio of hydrogen to the primary amine or ammonia is from 15 to 1 to 250 to 1.

14. Process in accordance with claim 1, wherein a retention time of the reactants above the respective catalyst beds is 0.01 to 15 seconds.

15. Process in accordance with claim 1, wherein pressure inside the reactor is 0.1 to 10 bar (0.01 to 1.0 MPa).

16. Process in accordance with claim 1, wherein said unisolated intermediate product is directly reacted with said primary amine or ammonia.

* * * * *

UNITED STATES PATENT AND TRADEMARK OFFICE
CERTIFICATE OF CORRECTION

PATENT NO. : 5,478,950
DATED : December 26, 1995
INVENTOR(S) : Manfred BERGFELD et al.

It is certified that error appears in the above-indentified patent and that said Letters Patent is hereby corrected as shown below:

On the cover page, in the ABSTRACT, line 4, after "amine", insert --or ammonia--;

line 6, delete "or ammonia".

Column 1, line 47, change "gammabutyrolactone" to --gamma-butyrolactone--;

line 65, change "gammabutyrolactone" to --gamma-butyrolactone--;

Column 2, line 5, change "arm." to --atm.--.

Column 4, claim 6, line 23, change "reaction" to --reactions--

UNITED STATES PATENT AND TRADEMARK OFFICE
CERTIFICATE OF CORRECTION

PATENT NO. : 5,478,950
DATED : December 26, 1995
INVENTOR(S) : Manfred BERGFELD et al.

It is certified that error appears in the above-indentified patent and that said Letters Patent is hereby corrected as shown below:

Column 4, claim 14, line 43, delete "a".

Signed and Sealed this

Nineteenth Day of March, 1996

*Attest:*

BRUCE LEHMAN

*Attesting Officer*  *Commissioner of Patents and Trademarks*